United States Patent [19]

Lang

[11] Patent Number: 5,206,256
[45] Date of Patent: Apr. 27, 1993

[54] NAPHTHALENE DERIVATIVES

[75] Inventor: Marc Lang, Rixheim, France

[73] Assignee: Ciba-Geigy Corporation, Ardsley, N.Y.

[21] Appl. No.: 687,802

[22] Filed: Apr. 19, 1991

[30] Foreign Application Priority Data

Apr. 20, 1990 [CH] Switzerland .......... 1339/90

[51] Int. Cl.$^5$ .......... A61K 31/41; C07D 249/08; C07D 249/12

[52] U.S. Cl. .......... 514/383; 514/384; 548/262.2; 548/263.2; 548/263.4; 548/263.6; 548/263.8; 548/264.2; 548/267.2; 548/267.4; 548/267.6; 548/267.8; 548/268.6; 548/269.4

[58] Field of Search .......... 514/383, 384; 548/262.2, 263.6, 263.2, 263.4, 263.8, 264.2, 267.2, 267.4, 267.6, 267.8, 268.6, 269.4

[56] References Cited

U.S. PATENT DOCUMENTS

| | | | |
|---|---|---|---|
| 3,407,210 | 10/1968 | Schoetensack et al. | 260/326 |
| 3,686,188 | 8/1972 | Huebner | 260/294.8 |
| 4,284,787 | 8/1981 | Knupfer et al. | 548/256 |
| 4,452,986 | 6/1984 | Johnson et al. | 548/336 |
| 4,749,713 | 6/1988 | Bowman et al. | 514/341 |
| 4,894,381 | 1/1990 | Schade et al. | 514/383 |
| 4,916,144 | 4/1990 | Strehlke et al. | 514/326 |
| 4,937,250 | 6/1990 | Bowman et al. | 514/341 |
| 4,978,761 | 12/1990 | Goto et al. | 549/462 |
| 5,021,444 | 6/1991 | Trada et al. | 514/397 |
| 5,071,861 | 12/1991 | Bowman et al. | 514/332 |
| 5,073,574 | 12/1991 | Lang | 514/381 |
| 5,098,911 | 3/1991 | Ibrahim | 514/300 |

FOREIGN PATENT DOCUMENTS

| | | |
|---|---|---|
| 4392389 | 11/1988 | Australia . |
| 054233 | 6/1982 | European Pat. Off. . |
| 073663 | 3/1983 | European Pat. Off. . |
| 165780 | 12/1985 | European Pat. Off. . |
| 165783 | 12/1985 | European Pat. Off. . |
| 165784 | 12/1985 | European Pat. Off. . |
| 207563 | 1/1987 | European Pat. Off. . |
| 277384 | 8/1988 | European Pat. Off. . |
| 293978 | 12/1988 | European Pat. Off. . |
| 296749 | 12/1988 | European Pat. Off. . |
| 316097 | 5/1989 | European Pat. Off. . |
| 363789 | 4/1990 | European Pat. Off. . |

OTHER PUBLICATIONS

Jones, et al. J. Med. Chem. 33:416 (1990).
Katrinsky, et al. Can. J. Chem. 66:1617 (1988).
Ashton, et al. J. Med. Chem. 27:1245 (1984).
Layton, et al. J. Chem. Soc. C:611 (1968).
Chem. Abs. 101:596 #90383h (1984).
Cross et al. J. Med. Chem. 29:1643 (1986).

Primary Examiner—Patricia L. Morris
Attorney, Agent, or Firm—Karen G. Kaiser; Irving M. Fishman

[57] ABSTRACT

Compounds of formula I

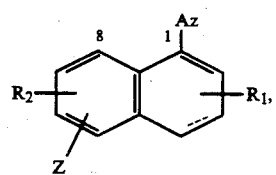

wherein the dotted line, Az, Z, $R_1$ and $R_2$ are as defined in the description, have valuable pharmaceutical properties and are effective especially against tumors. They are prepared in a manner known per se.

10 Claims, No Drawings

NAPHTHALENE DERIVATIVES

The invention relates to compounds of formula I

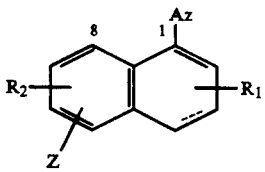

wherein the dotted line indicates the presence or absence of an additional bond, Az is heteroaryl bonded by way of a ring nitrogen atom, Z is a substituent other than hydrogen, and each of $R_1$ and $R_2$ independently of the other is hydrogen or one or more substituents other than hydrogen, with the proviso that neither Z nor $R_2$ is a substituent in the 8-position from the group consisting of hydroxy, unsubstituted or substituted alkenyloxy and unsubstituted or substituted alkynyloxy, and salts thereof, to processes for the preparation of those compounds, to pharmaceutical compositions comprising those compounds, and to the use of those compounds for the therapeutic treatment of the human or animal body or for the preparation of pharmaceutical compositions.

When the dotted line in formula I indicates the presence of an additional bond, the compounds are naphthalene derivatives; when the dotted line in formula I indicates the absence of an additional bond, the compounds are 3,4-dihydronaphthalene derivatives substituted in the 1-position.

Each of the radicals $R_1$ and $R_2$ independently of the other may be one or more substituents other than hydrogen. Each of the radicals $R_1$ and $R_2$ independently of the other is especially hydrogen or one or two—more especially one—substituent(s) other than hydrogen. hereinafter preferably have the following meanings:

Heteroaryl bonded by way of a ring nitrogen atom is a heterocyclic radical of aromatic nature which contains at least one ring nitrogen atom and is bonded by way of one of its ring nitrogen atoms. Such a radical is preferably imidazolyl or triazolyl each bonded by way of a ring nitrogen atom, but it may also be, for example, tetrazolyl, pyrazolyl, pyrrolyl, benzimidazolyl or benzotriazolyl each bonded by way of a ring nitrogen atom. All those radicals are preferably unsubstituted, but they may also be substituted, for example by lower alkyl, aryl-lower alkyl, trifluoromethyl, lower alkoxy, halogen and/or by hydroxy.

Imidazolyl bonded by way of a ring nitrogen atom is especially 1-imidazolyl, but may also be, for example, 1-imidazolyl substituted at ring carbon atoms, for example by lower alkyl or by aryl-lower alkyl.

Triazolyl bonded by way of a ring nitrogen atom is especially 1(1,2,4-triazolyl), 1(1,3,4-triazolyl) or 1-(1,2,3-triazolyl), but may also be, for example, 1-(1,2,5-triazolyl), or 1(1,2,4-triazolyl), 1-(1,3,4-triazolyl), 1(1,2,3-triazolyl) or 1(1,2,5-triazolyl) each substituted at ring carbon atoms, for example by lower alkyl or by aryl-lower alkyl.

Tetrazolyl bonded by way of a ring nitrogen atom is especially 1-tetrazolyl or 2-tetrazolyl, but may also be, for example, 1- or 2-tetrazolyl substituted in the 5-position, for example by lower alkyl or by aryl-lower alkyl.

A substituent other than hydrogen is, for example, lower alkyl, trifluoromethyl, cycloalkyl, aryl-lower alkyl, hydroxy, lower alkoxy, aryl-lower alkoxy, aryloxy; acyloxy, for example lower alkanoyloxy; halogen, amino, N-alkylamino, N,N-dialkylamino; acylamino, for example lower alkanoylamino; nitro, lower alkanoyl, arylcarbonyl, carboxy, lower alkoxycarbonyl, carbamoyl (—CONH$_2$), N-lower alkylcarbamoyl, N,N-di-lower alkylcarbamoyl, N-arylcarbamoyl, cyano, mercapto, lower alkylthio, lower alkylsulfonyl, sulfamoyl (—SO$_2$NH$_2$), N-lower alkylsulfamoyl or N,N-di-lower alkylsulfamoyl.

A substituent Z other than hydrogen is preferably carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl.

Aryl is, for example, phenyl or naphthyl, such as 1- or 2-naphthyl. The phenyl and naphthyl radicals may be unsubstituted or substituted, especially as indicated below for phenyl. Aryl is preferably phenyl that is unsubstituted or substituted by one or more, especially one or two, substituents from the group consisting of lower alkyl, lower alkoxy, hydroxy, lower alkanoyloxy, nitro, amino, halogen, trifluoromethyl, carboxy, lower alkoxycarbonyl, carbamoyl, N-lower alkylcarbamoyl, N,N-di-lower alkylcarbamoyl, cyano, lower alkanoyl, arylcarbonyl, lower alkylsulfonyl, sulfamoyl, N-lower alkylsulfamoyl and N,N-di-lower alkylsulfamoyl. Aryl is especially phenyl that is unsubstituted or substituted by lower alkyl, lower alkoxy, hydroxy, halogen, or by trifluoromethyl, and is most especially phenyl.

Arylcarbonyl is, for example, benzoyl that is unsubstituted or substituted by lower alkyl, lower alkoxy, hydroxy, halogen or by trifluoromethyl, and is especially benzoyl.

Aryl-lower alkyl is, for example, phenyl-lower alkyl and especially benzyl.

The term "lower" denotes a radical having up to and including 7, especially up to and including 4, and most especially 1 or 2, carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl.

Halogen is especially chlorine and bromine, but may also be fluorine or iodine.

Lower alkanoyl is, for example, formyl, acetyl, pripionyl or pivaloyl.

Cycloalkyl is preferably $C_3-C_8$cycloalkyl and especially $C_5-C_6$cycloalkyl, which is intended to mean that it contains from 3 to 8 and 5 or 6 ring carbon atoms, respectively. However, it may also be substituted, for example by lower alkyl.

Salts of compounds according to the invention are especially pharmaceutically acceptable, non-toxic salts. For example, compounds of formula I having basic groups can form acid addition salts, for example with inorganic acids, such a hydrochloric acid, sulfuric acid or phosphoric acid, or with suitable organic carboxylic or sulfonic acids, for example acetic acid, fumaric acid or methanesulfonic acid, or with amino acids, such as arginine or lysine. Compounds of formula I having an acid group, for example carboxy or 1-tetrazolyl, form, for example, metal salts or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis(2-hydroxyethyl)amine or tris(2-hydroxyethyl)amine, basic aliphatic esters of carboxylic acids, for example 4-aminobenzoic acid 2-diethylaminoethyl ester, lower alkyleneamines, for example 1-ethylpiperidine, cylcoalkylamines, for example dicylclohexylamine, or benzylamines, for example N,N'-dibenzylethylenediamine, dibenzylamine or benzyl-$\beta$-phenethylalmine. Compounds of formula I having an acid group and a basic group may also be in the form of internal salts, that is to say in zwitterionic form.

For the purpose of isolation or purification it is also possible to use pharmaceutically unacceptable salts, for example picrates or perchlorates. Only the pharmaceutically acceptable, non-toxic salts are used therapeutically, and these are therefore preferred.

The compounds of formula I according to the invention have valuable, especially pharmacologically acceptable, properties. In particular, they selectively inhibit the enzyme aromatase in mammals, including humans. As a result, the metabolic conversion of androgens to oestrogens is inhibited. The compounds of formula I are therefore suitable, for example, for the treatment of oestrogen-dependent diseases, including oestrogen-dependent breast cancer, especially in postmenopausal women. They are also useful, for example, in the treatment of gynaecomastia, i.e. breast development in males, since the aromatisation of the steroids is inhibited.

These effects can be demonstrated by in vitro tests or in vivo tests, preferably on mammals, for example guinea pigs, mice, rats, cats, dogs or apes. The dosage used is, for example, within a range of approximately from 0.001 to 10 mg/kg, preferably from 0.001 to 1 mg/kg.

The in vitro inhibition of aromatase activity can be demonstrated, for example, using the method described in J. Biol. Chem. 249, 5364 (1974). $IC_{50}$ values for aromatase inhibition can furthermore be obtained, for example, in vitro from enzyme-kinetic studies concerned with the inhibition of the conversion of 4-$^{14}$C-androstenedione to 4-$^{14}$C-oestrone in human placental microsomes. The $IC_{50}$ values of the compounds according to the invention are, at the minimum, about $10^{-9}$M.

In vivo, aromatase inhibition can be demonstrated, for example, by the suppression of the ovarian oestrogen content of female rats that are injected first with mare's serum gondotrophin and, two days later, with human chorionic gondotrophin, and treated p.o. the next day with a compound of the invention and, one hour later, with androstenedione. A further possible method of determining aromatase inhibition in vivo is described below: androstenedione (30 mg/kg subcutaneously) is administered on its own or together with a compound of the invention (orally or subcutaneously) for 4 days to sexually immature female rats. After the fourth administration, the rats are sacrificed and the uteri are isolated and weighed. The aromatase inhibition is determined by the extent to which the hypertrophy of the uterus caused by the administration of androstenedione on its own is suppressed or reduced by the simultaneous administration of the compound according to the invention. The minimum effective dose of the compounds of the invention is the in vivo tests is approximately from 0.001 to 1 mg/kg.

The anti-tumoral activity, especially in the case of oestrogen-dependent turmours, can be demonstrated in vivo, for example in DMBA-induced mammary tumours in female Sprague-Dawley rate [cf. Proc. Soc. Exp. Biol. Med. 160, 296–301 (1979)]. The use of compounds according to the invention brings about a regression of the tumours and furthermore suppresses the occurrence of new tumours at daily doses of about 1 mg/kg and above p.o.

In addition, the compounds of formula I do not have an inhibiting effect on the cleavage of the cholesterol side-chain and do not induce adrenal hypertrophy, as is demonstrated by investigation of the endocrine system.

On account of their pharmacological properties as extremely selective inhibitors of the enzyme aromatase, the compounds of formula I are suitable, for example, for the treatment of oestrogen-dependent diseases, such as breast tumours (breast carcinoma), endometriosis, premature labour or endometrial tumours in women, or of gynacomastia in men.

Preference is given to compounds of formula I wherein the dotted line indicates the presence or absence of an additional bond, Az is imidazoyl, triazolyl, tetrazolyl, pyrazolyl, pyrrolyl, benzimidazolyl or benzotriazolyl each bonded by way of a ring nitrogen atom, each of those radicals being unsubstituted or substituted ar carbon atoms by lower alkyl, aryl-lower alkyl, trifluoromethyl, lower alkoxy, halogen and/or by hydroxy, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and each of $R_1$ and $R_2$ independently of the other is hydrogen, lower alkyl, trifluoromethyl, $C_3$–$C_8$cycloalkyl, aryl-lower alkyl, hydroxy, lower alkoxy, aryl-lower alkoxy, aryloxy, lower alkanoyloxy, halogen, amino, N-alkylamino, N,N-dialkylamino, lower alkanoylamino, nitro, lower alkanoyl, arylcarbonyl, carboxy, lower alkoxycarbonyl, carbamoyl, N-lower akylcarbamoyl, N,N-di-lower alkylcarbamoyl, N-arylcarbamoyl, cyano, mercapto, lower alkylthio, lower alkylsulfonyl, sulfamoyl, N-lower alkylsulfamoyl or N,N-di-lower alkylsulfamoyl; in which aryl is phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, and salts thereof.

Preference is given especially to compounds of formula I wherein the dotted line indicates the presence or absence of an additional bond, Az is imidazolyl, triazolyl or tetrazolyl each bonded by way of a ring nitrogen atom, each of those radicals being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and each of $R_1$ and $R_2$ independently of the other is hydrogen, lower alkyl, lower alkoxy, hydroxy, halogen or trifluoromethyl; in which aryl is phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, and salts thereof.

Special preference is given to compounds of formula I wherein the dotted line indicates the presence or absence of an additional bond, Az is imidazolyl or triazolyl each bonded by way of a ring nitrogen atom, Z is carboxy, lower alkoxycarbonyl, carbamoyl, N-lower alkylcarbamoyl, N,N-di-lower alkylcarbamoyl, N-arylcarbamoyl, cyano, halogen, lower alkoxy, aryl-lower alkoxy, aryloxy or lower alkyl, in which aryl is in each case phenyl that is unsubstituted or substituted by one or two substituents from the group consisting of lower alkyl, lower alkoxy, hydroxy, halogen and trifluoromethyl, and each of $R_1$ and $R_2$ is hydrogen, and salts thereof.

Very special preference is given to compounds of formula I wherein the dotted line indicates the absence of an additional bond, Az is 1-imidazolyl, 1-(1,2,4-triazolyl), 1-(1,2,3-triazolyl) or 1-(1,3,4-triazolyl), Z is linked in the 5-, 6- or 7-position and is cyano, carbamoyl, N-arylcarbamoyl, halogen,. lower alkoxy, aryloxy or lower alkyl, in which aryl is phenyl that is unsubstituted or substituted by lower alkyl, lower alkoxy or by halogen, and each of $R_1$ and $R_2$ is hydrogen, and salts thereof.

Preference is given very especially to compounds of formula I wherein the dotted line indicates the absence of an additional bond, Az is 1-imidazolyl, 1-(1,2,4-triazolyl) or 1-(1,2,3-triazolyl), Z is linked in the 6-position and is cyano, carbamoyl, N-phenylcarbamoyl, chlorine, bromine, lower alkoxy, phenyloxy or lower alkyl, and each of $R_1$ and $R_2$ is hydrogen, and salts thereof.

Preference is given most especially to compounds of formula I wherein the dotted line indicates the absence of an additional bond, Az is 1-imidazolyl or 1(1,2,4-triazolyl), Z is linked in the 6-position and is cyano, carbamoyl, chlorine or bromine, and each of $R_1$ and $R_2$ is hydrogen, and salts thereof.

As sub-groups of a group of compounds of formula I, prominence is to be given to each of the following: (a) compounds of formula I wherein Z is linked in the 6-position; (b) compounds of the formula I wherein $R_1$ is hydrogen; (c) compounds of formula I wherein each of $R_1$ and $R_2$ is hydrogen; (d) compounds of formula I wherein the dotted line indicates the absence of an additional bond; and (e) compounds for formula I wherein the dotted line indicates the presence of an addition bond and Az is 1- or 2-tetrazolyl.

The invention relates most especially to the specific compounds described in the Examples and to pharmaceutically acceptable salts thereof.

The compounds of formula I can be prepared in a manner known per se, for example by (a) for the preparation of compounds of formula I wherein the dotted line indicates the absence of an additional bond, reacting a compound of formula II

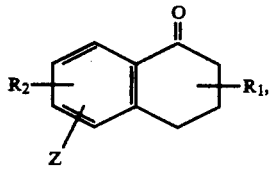
(II)

wherein Z, $R_1$ and $R_2$ are as defined under formula I, with a compound of formula III Az—H (III), wherein Az is as defined under formula I, or with an N-protected or activated derivative thereof, or (b) for the preparation of compounds of formula I wherein the dotted line indicates the absence of an additional bond, in a compound of formula IV

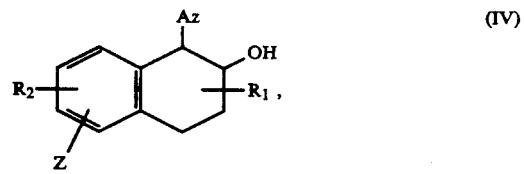
(IV)

wherein Az, Z, $R_1$ and $R_2$ are as defined under formula I, removing the elements of water, or (c) for the preparation of compounds of formula I wherein the dotted line indicates the presence of an additional bond, reacting a compound of formula V

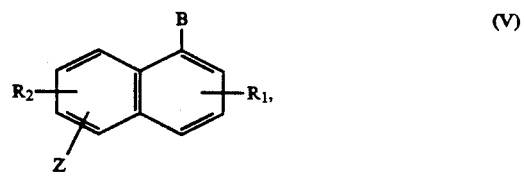
(V)

wherein Z, $R_1$ and $R_2$ are as defined under formula I and B is a substituent bonded by way of nitrogen, with a reagent that forms the azole ring Az, or (d) for the preparation of compounds of formula I wherein the dotted line indicates the presence of an additional bond, oxidising with an oxidising agent a corresponding compound of the formula I wherein the dotted line indicates the absence of an additional bond; and/or, if desired, converting a resulting compound of formula I into a different compound of formula I, and-/or, if desired, converting a resulting salt into the free compound or into a different salt, and/or, if desired, converting a resulting free compound of formula I into a salt, and/or separating a resulting mixture of isomeric compounds of formula I into the individual isomers.

In the following, more detailed description of processes (a), (b), (c) and (d), each of the symbols Az, Z, $R_1$ and $R_2$ is as defined under formula I, unless indicated to the contrary.

PROCESS (A)

If, in the reaction according to process (a), 1,2,4-triazole is used as the compound of formula III, the—depending upon the reaction conditions chosen—there are normally obtained mixtures of compounds of formula I wherein Az is 1-(1,2,4-triazolyl) and 1-(1,3,4-triazolyl), which can be separated, for example, by chromatography. Correspondingly, if 1,2,3-triazole is used as the compound of formula III, then there are normally obtained mixtures of compounds of formula I wherein Az is 1-(1,2,3-triazolyl) and 1(1,2,5-triazolyl), which can likewise be separated, for example, by chromatography. Correspondingly, it tetrazole is used as the compound of formula III, then there are normally obtained mixtures of compounds of formula I wherein Az is 1-tetrazolyl and 2-tetrazolyl, which can likewise readily be separated, for example, by chromatography.

In many cases it is possible, by using compounds of formula III in which a specific ring nitrogen atom has been protected by a protecting group, to obtain selectively only one of the two compounds in question.

N-protected derivatives of compounds of formula III are therefore compounds of formula III wherein a ring nitrogen atom has been protected by a suitable protecting group, for example tri-lower alkylsilyl, for example trimethylsilyl, lower alkanoyl, for example acetyl, N,N-di-lower alkylcarbamoyl, for example N,N-dimethylcarbamoyl, or triarylmethyl, for example, triphenylmethyl.

Prior to the reaction according to process (a), the compounds of formula III are preferably converted into an activated derivative, which permits selective production of a specific radical Az in the compounds of formula I.

Activated derivatives of compounds of formula III are, for example, the sulfoxides of the formula Az—SO—Az which are obtained, for example, after reaction of compounds of formula III with thionyl chloride, especially di(1-imidazolyl)sulfoxide or di-[1(1,2,4-triazolyl)] sulfoxide.

The condensation reaction according to process (a) is known per se and corresponds to the reaction of a ketone with a secondary amine with (formal) enamine formation. This reaction is carried out, for example, without the addition of bases or, preferably, in the presence of bases, for example potassium carbonate, sodium, triethylamine or pyridine.

The starting compounds of formula II (1-tetralones) are known per se or are prepared analogously to the known compounds.

Substituted 1-tetralones can be prepared, for example, by oxidation, for example with chromium trioxide (CrO₃), from correspondingly substituted tetralines of formula VI

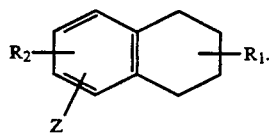

(VI)

Substituted 1-tetralones can also be prepared, for example, by intramolecular Friedel-Crafts acylation of 4-phenylbutanoic acids of formula VII

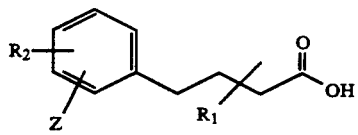

(VII)

or acid derivatives thereof, for example acid chlorides or acid anhydrides. As catalysts there may be used in the case of free acids for example polyphosphoric acid and in the case of acid chlorides or anhydrides for example AlCl₃.

Substituents Z, R₁ and R₂ that are not stable under the conditions of 1-tetralone syntheses must be either (a) protected beforehand by a protecting group, which is removed after the 1-tetralone synthesis has been carried out [or after process (a) has been carried out], or (b) produced after the 1-tetralone synthesis from other groups that are stable under the conditions of 1-tetralone syntheses, according to known reaction methods. It is also possible to combine the two methods (a) and (b); for example, in the case of aminotetralines of formula VI it is advantageous to protect the amino groups, then carry out oxidation to form the 1-tetralone and remove the amino-protecting group. Then—if desired—the amino group can be diazotised and converted in known manner into any one of a large number of other radicals Z.

Suitable amino-protecting groups are, for example, acyl, such as lower alkanoyl, for example acetyl, or N,N-di-lower alkylcarbamoyl, for example N,N-dimethylcarbamoyl; silyl, such as tri-lower alkylsilyl, for example trimethylsilyl; or triarylmethyl, for example triphenylmethyl.

Protecting groups and the methods by which they are introduced and removed are described, for example, in "Protective Groups in Organic Chemistry", Plenum Press, London, N.Y. 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981, A characteristic of protecting groups is that they can be removed readily, that is to say without undesired secondary reactions taking place, for example by solvolysis, by reduction or by photolysis.

PROCESS (B)

The elimination of water from compounds of formula IV can take place either directly, for example by reaction with acids, for example phosphoric acid, or, preferably, indirectly via intermediate steps. For example, the hydroxy group can first be converted into a tosyloxy, mesyloxy or halogen radical; after treatment with a strong base, for example potassium tert-butoxide or DBU [1,8-diazabicyclo[5.4.0] undec-7-ene (1.5-5)], the desired compounds of formula I wherein the dotted line indicates the absence of an additional bond are obtained.

The starting compounds of formula IV are obtained, for example, by reacting a compound of formula VII

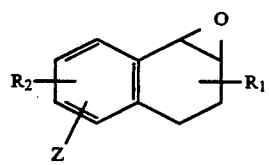

(VIII)

with a compound of formula III, Az—H. The compound of formula III is preferably used in the form of an alkali metal salt, for example sodium salt, which is obtainable, for example, by reacting Az—H with sodium hydride.

The compounds of formula VIII are prepared, for example, by epoxidizing the corresponding olefin, that is to say a compound of formula IX

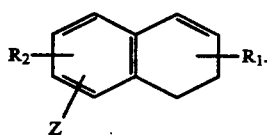

(IX)

A suitable reagent for that purpose is, for example, m-chloroperbenzoic acid.

The compounds of formula IX are obtainable, for example, by elimination of water from the 1-hydroxytetralines of formula X

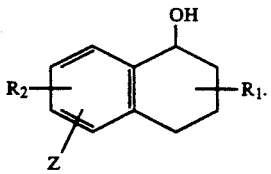

(X)

The compounds of formula X in turn can be prepared, for example, by reduction of the corresponding 1-tetralones of formula II, for example with sodium borohydride.

PROCESS (C)

A substituent B bonded by way of nitrogen is especially amino, but may also be, for example, isocyano (—N≡C), hydrazino or azido.

A reagent that forms the azole ring Az reacts with the radical B to form the desired radical Az. The ring that is formed initially may still contain readily removable substituents, for example carboxy groups, which can readily be removed by a decarboxylation step. In detail, the radicals Az an be prepared from the substituents B, for example, as follows:

1. B=isocyano; reaction with hydrazoic acid or, especially, an alkali metal salt thereof, e.g. sodium azide; yields Az=1-tetrazolyl (see Tetrahedron Lett. 1969, 5081)

2. B=amino; reaction with dimethoxyethyl isothiocyanate [(CH$_3$O)$_2$CH—CH$_2$—N=C=S] according to J. Chem Soc. 127, 581 (1925), then acid hydrolysis, for example, with HCl in ethylene glycol and desulfurisation with Raney nickel (see J. Chem. Soc. Chem. Commun. 1989, 898); yields Az=1-imidazolyl 3. B=azido; 1,3-dipolar cycloaddition (a) with acetylenedicarboxylic acid and decarboxylation of the two carboxy groups or (b) with acetylene [see Bull. Soc. Chim. Belges 79, 195 (1970)]; yields Az=1-(1,2,3-triazolyl)

4. B=hydrazino; reaction with the imino ether C$_2$H$_5$O—CH=NH$_2$⊕Cl⊖ [see J. Org. Chem. 37, 3504 (1972)]; yields Az=1-(1,2,4-triazolyl)

5. B=amino; reaction with (a) s-diformylhydrazine and ZnCl$_2$[see Ber. 32, 797 (1889)] or (b) N,N-dimethylformamide-azine hydrochloride [(CH$_3$)$_2$N—CH=N—N=CH—N(CH$_3$)$_2$.HCl], formed by reaction of hydrazine, DMF and thionyl chloride [see J. Org. Chem. 18, 1368 (1953) and J. Chem. Soc. C 1967, 1664]; yields 1-(1,3,4-triazolyl)

The naphthalene starting compounds of formula V are known per se or can be prepared analogously to the known compounds. In particular, the 1-aminonaphthalenes of formula V (B=NH$_2$) can be obtained from the corresponding 1-tetralones of formula II by first converting the latter into the corresponding oximes, for example by reaction with hydroxylamine or a salt thereof in an acidic medium, and the reacting those oximes, for example, with glacial acetic acid, acetic acid anhydride and HCl gas [see Ber. Dtsch. Chem. Ges. 1930, 1318].

A further possible method of preparing compounds of formula V is the mononitration of 1- or, especially, 2-naphthylamine with concentrated sulfuric acid in the presence of urea (for example according to J. Chem. Soc. 1939, 348), which yields 5-nitro-1-(or 2-)naphthylamines. In the latter compounds the amino group can be diazotised and converted into any one of a large number of other substituents Z. Finally, the nitro group is converted into amino by reduction, for example by hydrogenation or with SnCl$_2$.

PROCESS (D)

Suitable oxidising agents for the conversion of dihydronaphthlenes into naphthalenes are, for example, manganese dioxide, DDQ [2,3-dichloro-5,6-dicyano-1,4-benzoquinone], sulfur or chloranil [2,3,5,6-tetrachloro-1,4-benzoquinone].

Compounds of formula I can be converted in a manner known per se into other compounds of formula I.

For example, compounds of formula I wherein Z is halogen, especially bromine, can be converted by reaction with a cyanating agent, for example cooper(I) cyanide, into other compounds of formula I wherein Z is cyano.

It is also possible, for example, to convert compounds of formula I wherein Z is halogen, especially bromine, by reaction with hydroxyaryl compounds or corresponding alkali metal salts thereof, for example potassium phenolate, into other compounds of formula I wherein Z is aryloxy, advantageously, for example, in the presence of copper.

Furthermore, for example, compounds of formula I wherein Z is cyano can be converted by partial hydrolysis, for example with potassium carbonate and aqueous H$_2$O$_2$ solution, into other compounds of formula I wherein Z is carbamoyl.

On the other hand, for example, compounds of formula I wherein Z is carbamoyl or N-lower alkylcarbamoyl can also be converted, with the removal of water or lower alkanol, respectively, into compounds of formula I wherein Z is cyano.

Free compounds of formula I having salt-forming properties that are obtainable according t the process can be converted into their salts in a manner known per se: compounds having basic properties, for example by treatment with acids or suitable derivatives thereof, and compounds having acid properties, for example by treatment with bases or suitable derivatives thereof.

Mixtures of isomers obtainable according to the invention can be separated into the individual isomers in a manner known per se: racemates, for example, by forming salts with optically pure salt-forming reagents and separating the diastereoisomeric mixture so obtainable, for example by means of fractional crystallisation.

The reactions described above can be carried out under conditions that are known per se, in the absence or, usually, in the presence of solvents or diluents, preferably those solvents or diluents which are inert towards the reagents used and are solvents therefor, in the absence or presence of catalysts, condensing agents or neutralising agents, and, depending upon the nature of the reaction and/or of the reactants, at reduced, normal or elevated temperature, for example within a temperature range of from approximately −70° C. to approximately 200° C., preferably from approximately −20° C. to approximately 150° C., for example at the boiling point of the solvent used, under atmospheric pressure or in a closed vessel, where appropriate under pressure, and/or in an inert atmosphere, for example under a nitrogen atmosphere.

In view of the close relationship between the compounds of formula I in free form and in the form of salts, hereinbefore and hereinafter any reference to the free compounds or their salts should be understood as including also the corresponding salts or free compounds, respectively, where appropriate and expedient.

The compounds, including their salts, may also be obtained in the form of hydrates, or their crystals may, for example, include the solvent used for crystallisation. The starting materials used in the compounds described at the beginning as being especially valuable.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt thereof.

The present invention relates also to pharmaceutical compositions that comprise one of the pharmacologically active compounds of formula I as active ingredient. Compositions for enteral, especially oral, administration and for parenteral administration are especially preferred. The compositions comprise the active ingredient on its own or, preferably, together with a pharmaceutically acceptable carrier. The dosage of the active ingredient depends upon the disease to be treated and upon the species, its age, weight and individual condition, and also upon the mode of administration.

The pharmaceutical compositions comprise from approximately 0.01% to approximately 95% active ingredient, dosage forms that are in single-dose form preferably comprising from approximately 1% to approximately 90% active ingredient, and dosage forms that are not in single-dose form preferably comprising from approximately 0.1% to approximately 20% active ingredient. Unit dose forms, such as dragées, tablets or capsules, comprise from approximately 0.5 mg to approximately 100 mg of active ingredient.

The pharmaceutical compositions of the present invention are prepared in a manner known per se, for example by means of conventional mixing, granulating, confectioning, dissolving or lyophilising processes. For example, pharmaceutical compositions for oral administration can be obtained by combining the active ingredient with one or more solid carriers, if desired granulating a resulting mixture and, if desired, processing the mixture or granules into tablets or dragée cores, where appropriate by adding additional excipients.

Suitable carries are especially fillers, such as sugars, for example lactrose, saccharose, mannitol or sorbitol, cellulose preparations and/or calcium phosphates, for example tricalcium phosphate or calcium hydrogen phosphate, and binders, such as starches, for example corn, wheat, rice or potato starch, methylcelullose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silica, talc, stearic acid or salt thereof, such as magnesium or calcium stearate, and/or polyethylene glycol, or derivatives thereof.

Dragée cores may be provided with suitable, optionally enteric, coatings, there being used, inter alia, concentrated sugar solutions which may contain gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and, if desired, stabilisers. In soft capsules, the active ingredient is preferably dissolved or suspended in suitable liquid excipients, such as fatty oils, paraffin oil or liquid polyethylene glycols, to which stabilisers may also be added.

Other oral dosage forms are, for example, syrups prepared in customary manner that comprise the active ingredient, for example, in suspended form and in a concentration of approximately from 0.01% to 2%, preferably approximately 0.1% or in a similar concentration that provides a suitable single dose, for example, when administered in measures of 5 or 10 ml. Also suitable, for example, are powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, also stabilisers. In this case, the active ingredient, if desired together with excipients, may also be in the form of a lyophilisate and can be made into a solution by the addition of suitable solvents before parenterial administration.

Solutions, such as are used, for example, for parenteral administration, can also be used as infusion solutions.

The invention relates also to a method for the treatment of the pathological conditions mentioned above. The compounds of the present invention can be administered prophylactically or therapeutically, and are preferably used in the form of pharmaceutical compositions. For a body weight of approximately 70 g, a daily dose of from approximately 0.5 mg to approximately 100 mg, preferably from approximately 1 mg to approximately 20 mg, of a compound of the present invention is administered. The following Examples illustrate the present invention; temperatures are given in degrees Celsius. The following abbreviations are used: ether=-diethyl ether; hexane=n-hexane; DMSO=dimethyl sulfoxide; TLC=thin-layer chromatography.

EXAMPLE 1

6-Cyano-1-(1-imidazolyl)-3,4-dihydronaphthalene

175 µl of thionyl chloride are added dropwise to a solution of 272 mg of imidazole in 2.5 ml of methylene chloride. 342 mg of 6-cyano-1-tetralone are added in portions to the resulting white suspension, and the reaction mixture is stirred for 7 hours at 40° and then for 24 hours at room temperature. 386 mg of potassium carbonate in 1.6 ml of water are added to the reaction mixture, which is then extracted with chloroform. After drying the organic phase over sodium sulfate, concentration is carried out under reduced pressure. The resulting crude product is purified by column chromatography (0.04–0.063 mesh SIO$_2$, hexane/ethyl acetate 1:2). Crystallisation from ether yields the title compound in the form of colourless crystals; m.p. 152°–153°. TLC (ethyl acetate): Rf=0.17.

EXAMPLE 2

Cyano-1-[1-(1,2,4-triazolyl)]-3,4-dihydronaphthalene

175 μl of thionyl chloride are added dropwise to a solution of 276 mg of 1,2,4-triazole in 2.5 ml of methylene chloride. After stirring for 5 minutes at room temperature, 342 mg of 6-cyano-1-tetralone are added, and the orange-coloured suspension is stirred for a further 6 days at the same temperature. A solution of 386 mg of potassium carbonate in 1.6 ml of water is then added to the reaction mixture, which is then extracted with chloroform. The organic phase is separated off, dried over sodium sulfate and concentrated. Column chromatography (SiO$_2$, hexane/ethyl acetate 1:2) yields the title compound, which is recrystallised from ether; m.p. 169°–170°. IR (CH$_2$Cl$_2$): 2220, 1495, 1430 cm$^{-1}$.

EXAMPLE 3

6-Chloro-1-(1-imidazolyl)-3,4-dihydronaphthalene 0.218 ml of thionyl chloride is added within a period of 15 minutes to a solution of 815 mg of imidazole in 3.2 ml of methylene chloride. At the end of the exothermic reaction, 451 mg of 6-chloro-1-tetralone are added to the resulting suspension. After stirring for 20 hours at room temperature, 497 mg of potassium carbonate in 2 ml of water are added, and the mixture is extracted twice with chloroform. After drying the organic extracts over sodium sulfate, concentration is carried out under reduced pressure. The resulting crude product is purified by column chromatography (SiO$_2$, 0.04–0.063 mesh, 0.15 bar, ethyl acetate); m.p. (after dry crystallisation from ether) 68°–72°.

EXAMPLE 4

6-Carbamoyl-1-(1-imidazolyl)-3,4-dihydronaphthalene

Potassium carbonate and 30% aqueous H$_2$O$_2$ solution are added several times, within a period of 24 hours, to 6-cyano-1-(1-imidazolyl)-3,4-dihydronaphthalene (Example 1) in DMSO and CH$_2$Cl$_2$. Finally, water is added and the solid is filtered off, yielding the title compound.

EXAMPLE 5

6-Carbamoyl-1-[1-(1,2,4-triazolyl)]-3,4-dihydronaphthalene

Potassium carbonate and 30% aqueous H$_2$O$_2$ solution are added several times, within a period of 20 hours, to 6-cyano-1-[1-(1,2,4-triazolyl)]-3,4-dihydronaphthalene (Example 2) in DMSO and methylene chloride. Finally, water is added and the solid is filtered of, yielding the title compound.

EXAMPLE 6

6-Bromo-1-(1-imidazolyl)-3,4-dihydronaphthalene

Analogously to Example 1, 6-bromo-1-tetralone is converted into the title compound.

EXAMPLE 7

6-Bromo-1-[1-(1,2,4-triazolyl)]-3,4-dihydronaphthalene

Analogously to Example 2, 6-bromo-1-tetralone is converted into the title compound.

EXAMPLE 8

6-Cyano-1-[1-(1,2,3-triazolyl)]-3,4-dihydronaphthalene

Analogously to Example 1, 6-cyano-1-tetralone is converted by reaction with 1,2,3-triazole and thionyl chloride into the title compound.

EXAMPLE 9

6-Bromo-1-[1-(1,2,3-triazolyl)]-3,4-dihydronaphthalene

Analogously to Example 8, 6-bromo-1-tetralone is converted into the title compound.

EXAMPLE 10

6-Cyano-1-(1-imidazolyl)-3,4-dihydronaphthalene 6-bromo-1-(1-imidazolyl)-3,4-dihydronaphthalene (Example 6) is converted by reaction with CuCN in 1-methylpyrrolidone into the title compound, m.p. 152°–153°.

EXAMPLE 11

6-Bromo-1-(1-imidazolyl)-3,4-dihydronaphthalene

Analogously to Example 1, 2.25 g of 6-bromo-1-tetralone are reacted with 1.36 g of imidazole and 0.873 ml of thionyl chloride, yielding the title compound, which is purified by column chromatography (SiO$_2$, hexane/ethyl acetate 9:1 to 1:1) and crystallisation from hexane/ether; m.p. 58°–64°, $^1$H-NMR (CDCl$_3$): δ (ppm)=0.43 (m, 2H), 2.9 (m, 2H), 6.12 (t, 2H), 6.63 (d, 1H), 7.02 (d, 1H), 7.18 (d, 1H), 7.28 (dd, 1H), 7.36 (d, 1H), 7.61 (s, 1H).

EXAMPLE 12

10,000 tablets are prepared, each comprising 5 mg of active ingredient, for example one of the compounds prepared in Example 1–11:

| Composition: | |
|---|---|
| active ingredient | 50.00 g |
| lactose | 2535.00 g |
| corn starch | 125.00 g |
| polyethylene glycol 6000 | 150.00 g |
| magnesium stearate | 40.00 g |
| purified water | quantum satis |

Procedure

All the pulverulent constituents are sieved through a sieve of 0.6 mm mesh size. Then the active ingredient, the lactose, the magnesium stearate and half of the starch are mixed in a suitable mixer. The other half of the starch is suspended in 65 ml of water and the resulting suspension is added to a boiling solution of the polyethylene glycol in 260 ml of water. The paste formed is added to the powder mixture and the resulting mixture is granulated, if desired or necessary with the addition of more water. The granules are dried overnight at 35° C., forced through a sieve of 1.2 mm mesh size and pressed into tablets having a breaking notch.

EXAMPLE 13

1000 capsules are prepared, each comprising 10 mg of active ingredient, for example one of the compounds prepared in Examples 1-11:

| Composition: | |
|---|---|
| active ingredient | 10.00 g |
| lactose | 207.00 g |
| modified starch | 80.00 g |
| magnesium stearate | 3.00 g |

Procedure

All the pulverulent constituents are sieved through a sieve of 0.6 mm mesh size. Then, in a suitable mixer, the active ingredient is mixed first with the magnesium stearate and then with the lactose and the starch until homogenous. No. 2 hard gelatin capsules are each filled with 300 mg of the resulting mixture using a capsule-filling machine.

What is claimed is:

1. A compound of formula I

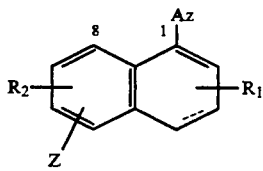

wherein the dotted line indicates the presence or absence of an additional bond, Az is 1,2,4-triazolyl bonded by way of a ring nitrogen atom, said triazolyl being unsubstituted or substituted at carbon atoms by lower alkyl, aryl-lower alkyl, trifluoromethyl, lower alkoxy, halogen or hydroxy, Z is $C_3$-$C_8$cycloalkyl, aryl-lower alkyl, hydroxy, aryl-lower alkoxy, aryloxy; lower alkanoyloxy; amino; lower alkanoylamino; nitro, lower alkanoyl, arylcarbonyl, carboxy, lower alkoxycarbonyl, carbamoyl, N-lower alkylcarbamoyl, N,N-di-lower alkylcarbamoyl, N-arylcarbamoyl, cyano, mercapto, lower alkylthio, lower alkylsulfonyl, sulfamoyl, N-lower alkylsulfamoyl or N,N-di-lower alkylsulfamoyl, and each of $R_1$ and $R_2$ independently of the other is hydrogen or one or more of the substituents selected from lower alkyl, trifluoromethyl, $C_3$-$C_8$cycloalkyl, aryl-lower alkyl, hydroxy, lower alkoxy, aryl-lower alkoxy, aryloxy; lower alkanoyloxy; halogen, amino; lower alkanoylamino; nitro, lower alkanoyl, arylcarbonyl, carboxy, lower alkoxycarbonyl, carbamoyl, N-lower alkylcarbamoyl, N,N-di-lower alkylcarbamoyl, N-arylcarbamoyl, cyano, mercapto, lower alkylthio, lower alkylsulfonyl, sulfamoyl, N-lower alkylsulfamoyl or N,N-di-lower alkylsulfamoyl, with the provision that neither Z nor $R_2$ is a hydroxy substituent in the 8-position, or a salt thereof; in which aryl is phenyl or naphthyl which may be unsubstituted or substituted by one or two substituents from the group consisting of lower alkyl, lower alkoxy, hydroxy, lower alkanoyloxy, nitro, amino, halogen, trifluoromethyl, carboxy, lower alkoxycarbonyl, carbamoyl, N-lower alkylcarbamoyl, N,N-di-lower alkylcarbamoyl, cyano, lower alkanoyl, lower alkylsulfonyl, sulfamoyl, N-lower alkylsulfamoyl and N,N-di-lower alkylsulfamoyl.

2. A compound of formula I according to claim 1 wherein the dotted line indicates the presence or absence of an additional bond, Az is 1,2,4-triazol-1-yl being unsubstituted or substituted at carbon atoms by lower alkyl, aryl-lower alkyl, trifluoromethyl, lower alkoxy, halogen and/or by hydroxy, Z is carboxy, lower alkoxycarbonyl, carbamoyl, N-lower alkylcarbamoyl, N,N-di-lower alkylcarbamoyl, N-arylcarbamoyl, cyano, hydroxy, aryl-lower alkoxy, aryloxy or aryl-lower alkyl, and each of $R_1$ and $R_2$ independently of the other is hydrogen, lower alkyl, trifluoromethyl, $C_3$-$C_8$cycloalkyl, aryl-lower alkyl, hydroxy, lower alkoxy, aryl-lower alkoxy, aryloxy, lower alkanoyloxy, halogen, amino, lower alkanoylamino, nitro, lower alkanoyl, arylcarbonyl, carboxy, lower alkoxycarbonyl, carbamoyl, N-lower alkylcarbamoyl, N,N-di-lower alkylcarbamoyl, N-arylcarbamoyl, cyano, mercapto, lower alkylthio, lower alkylsulfonyl, sulfamoyl, N-lower alkylsulfamoyl or N,N-di-lower alkylsulfamoyl; in which aryl is phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, or a salt thereof.

3. A compound of formula I according to claim 1 wherein the dotted line indicates the presence or absence of an additional bond, Az is 1,2,4-triazol-1-yl bonded by way of a ring nitrogen atom being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, hydroxy, aryl-lower alkoxy, aryloxy, or aryl-lower alkyl, and each of $R_1$ and $R_2$ independently of the other is hydrogen, lower alkyl, lower alkoxy, hydroxy, halogen or trifluoromethyl; in which aryl is phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, or a salt thereof.

4. A compound of formula I according to claim 1 wherein the dotted line indicates the presence or absence of an additional bond, Az is 1,2,4-triazol-1-yl, Z is carboxy, lower alkoxycarbonyl, carbamoyl, N-lower alkylcarbamoyl, N,N-di-lower alkylcarbamoyl, N-arylcarbamoyl, cyano, aryl-lower alkoxy or aryloxy, in which aryl is in each case phenyl that is unsubstituted or substituted by one or two substituents from the group consisting of lower alkyl, lower alkoxy, hydroxy, halogen and trifluoromethyl, and each of $R_1$ and $R_2$ is hydrogen, or a salt thereof.

5. A compound of formula I according to claim 1 wherein the dotted line indicates the absence of an additional bond, Az is 1-(1,2,4-triazolyl) Z is linked in the 5-, 6- or 7-position and is cyano, carbamoyl, N-arylcarbamoyl, or aryloxy, in which aryl is phenyl that is unsubstituted or substituted by lower alkyl, lower alkoxy or by halogen, and each of $R_1$ and $R_2$ is hydrogen, or a pharmaceutically acceptable salt thereof.

6. A compound of formula I according to claim 1 wherein the dotted line indicates the absence of an additional bond, Az is 1-(1,2,4-triazolyl), Z is linked in the 6-position and is cyano, carbamoyl, N-phenylcarbamoyl or phenyloxy, and each of $R_1$ and $R_2$ is hydrogen, or a pharmaceutically acceptable salt thereof.

7. A compound of formula I according to claim 1 wherein the dotted line indicates the absence of an additional bond, Az is 1-(1,2,4-triazolyl), Z is linked in the 6-position and is cyano or carbamoyl, and each of $R_1$ and $R_2$ is hydrogen, or a pharmaceutically acceptable salt thereof.

8. 6-Cyano-1-[1-(1,2,4-triazolyl)]-3,4-dihydronaphthalene according to claim 1, or a pharmaceutically acceptable salt thereof.

9. A pharmaceutical composition suitable for administration to a mammal for the treatment or prevention of a condition responsive to aromatase inhibition, comprising an effective aromatase inhibiting amount of a compound of formula I according to claim 1 and at least one pharmaceutically acceptable carrier.

10. A method for treating a disease responsive to aromatase inhibition comprising administering a therapeutically effective aromatase inhibiting amount of a compound of formula I according to claim 1 to an animal in need thereof.

* * * * *